United States Patent [19]

Bastian

[11] 4,137,323
[45] Jan. 30, 1979

[54] ORGANIC COMPOUNDS

[75] Inventor: Jean-Michel Bastian, Therwil, Switzerland

[73] Assignee: Sandoz Ltd., Basel, Switzerland

[21] Appl. No.: 809,666

[22] Filed: Jun. 24, 1977

Related U.S. Application Data

[60] Division of Ser. No. 673,257, Apr. 2, 1976, Pat. No. 4,052,412, and a continuation-in-part of Ser. No. 644,816, Dec. 29, 1975, abandoned, which is a continuation of Ser. No. 511,994, Oct. 4, 1974, abandoned.

[30] Foreign Application Priority Data

May 22, 1975 [CH] Switzerland .......... 6582/75

[51] Int. Cl.² .......... A01N 9/00; C07D 333/24; C07D 333/16
[52] U.S. Cl. .......... 424/275; 260/332.2 A; 260/332.3 R
[58] Field of Search .......... 260/332.2 A, 332.3 R; 424/275

[56] References Cited

U.S. PATENT DOCUMENTS 4,052,412 10/1977 Bastian .......... 260/332.2 A

Primary Examiner—A. Siegel
Attorney, Agent, or Firm—Gerald D. Sharkin; Robert S. Honor; Thomas O. McGovern

[57] ABSTRACT

This invention provides new compounds of formula I,

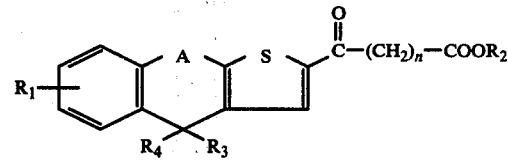

wherein
$R_1$ is hydrogen, halogen of atomic number from 9 to 35 or lower alkyl,
$R_2$ is hydrogen or lower alkyl, each of
$R_3$ and $R_4$ is hydrogen, or
$R_3$ and $R_4$ together are oxygen,
n is 2, 3 or 4, and
A is ethylene or vinylene,
useful as antiphlogistics and anti-arthritics.

17 Claims, No Drawings

ORGANIC COMPOUNDS

This is a division of application Ser. No. 673,257 filed Apr. 2, 1976, which issued as U.S. Pat. No. 4,052,412 on Oct. 4, 1977, and a continuation-in-part of our copending application Ser. No. 644,816, filed Dec. 29, 1975, now abandoned which in turn is a continuation of Ser. No. 511,994, filed Oct. 4, 1974 and now abandoned.

The present invention relates to new heterocyclic compounds.

In accordance with the invention there are provided new compounds of formula I,

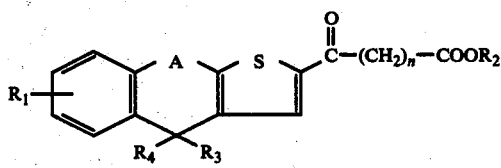

wherein
$R_1$ is hydrogen, halogen of atomic number from 9 to 35 or lower alkyl,
$R_2$ is hydrogen or lower alkyl, each of
$R_3$ and $R_4$ is hydrogen, or
$R_3$ and $R_4$ together are oxygen,
n is 2, 3 or 4, and
A is ethylene or vinylene.

Further, in accordance with the invention a compound of formula I may be obtained by a process comprising
(a) reacting a compound of formula II,

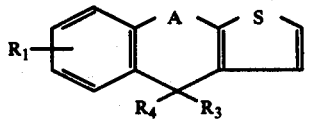

wherein $R_1$, $R_3$, $R_4$ and A are as defined above, with a compound of formula III,

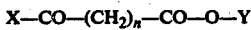     III wherein
n is as defined above,
X is chlorine or bromine, and
Y is lower alkyl, or
X and Y together form a bond,
or
(b) hydrolyzing a compound of formula Ib,

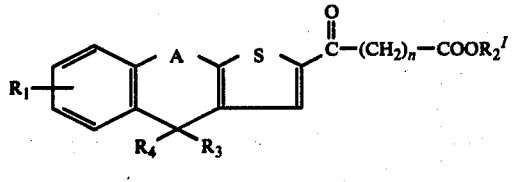

wherein
$R_1$, $R_3$, $R_4$, A and n are as defined above, and
$R_2^I$ is lower alkyl,
to produce a compound of formula Ia,

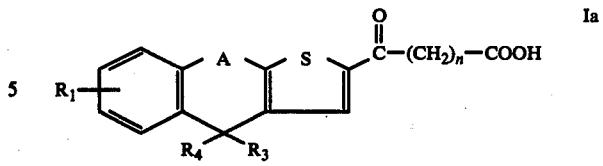

wherein $R_1$, $R_3$, $R_4$, A and n are as defined above.

In the compounds of formula I $R_1$ preferably signifies hydrogen or chlorine. $R_1$ is preferably present in the 6 or 7 position of the ring structure. When $R_1$ is lower alkyl, this preferably contains 1 to 4 carbon atoms and especially signifies methyl. The substituent $R_2$ preferably signifies hydrogen. When $R_2$ is lower alkyl, this contains, for example, 1 to 4 carbon atoms and especially signifies methyl or ethyl. $R_3$ and $R_4$ together preferably signify oxygen, and n preferably denotes 2.

Any carbon-containing radical not particularly defined herein preferably has up to 5 carbon atoms.

The reaction of a compound of formula II with a compound of formula III in accordance with process variant (a) is preferably effected in the presence of an acid condensation agent. In accordance with a preferred method of the process the reaction may, for example, be effected in the presence of a Lewis acid in an inert organic solvent, e.g. a chlorinated hydrocarbon such as methylene chloride or tetrachloroethane, or in carbon disulphide. A Friedel-Crafts reaction may be used.

Examples of suitable Lewis acids are aluminium trichloride or tin tetrachloride. The reaction of a compound of formula II with a compound of formula III may alternatively be effected in the presence of a strong mineral acid, e.g. polyphosphoric acid or phosphoric acid. There may be present an inert organic solvent, e.g. a hydrocarbon such as benzene, toluene, xylene or tetraline. When the reaction is effected in the presence of a Lewis acid, the reaction temperature preferably is between room temperature and the boiling temperature of the reaction mixture. The reaction in the presence of a strong mineral acid is preferably effected at a temperature between about 50° and 150° C. In the case of the reaction in the presence of a strong mineral acid any ester groupings —$COOR_2^I$, which may be present, may be simultaneously hydrolyzed, so that compounds of formula Ia are obtained.

The hydrolysis of an ester of formula Ib in accordance with process variant (b) may be effected in accordance with the usual methods for ester hydrolysis. For example, a compound of formula Ib may be hydrolyzed in the presence of a base, e.g. an alkali metal or alkaline earth metal hydroxide, or in the presence of an acid catalyst, e.g. a mineral acid such as hydrochloric acid or sulphuric acid, or an organic sulphonic acid. The hydrolysis may be effected at a temperature between room temperature and about 100° C. An inert water-miscible organic solvent may be present. The hydrolysis is preferably effected in an alkaline medium, e.g. with at least an equivalent amount of an aqueous alkali metal hydroxide solution at room temperature or at a slightly elevated temperature. Examples of organic solvents which may be present are lower alcohols, acetone or cyclic ethers such as tetrahydrofuran or dioxane.

The compounds of formula I may be isolated from the reaction mixture and purified in known manner. Free acid forms of formula Ia may be converted into salt forms thereof and vice versa. A suitable salt is the sodium salt.

The compounds of formula IIa,

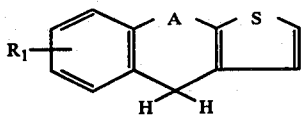

wherein $R_1$ and A are as defined above, used as starting materials, may, for example, be obtained by reducing a compound of formula IIb,

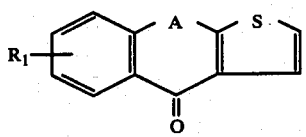

wherein $R_1$ and A are as defined above. The reduction may, for example, be effected in accordance with Clemmensen with amalgamated zinc/hydrochloric acid, or, when A is an ethylene group, also by treatment with sodium/alcohol.

Insofar as the production of the starting materials is not described, these are known or may be produced in accordance with known processes, or in a manner analogous to the processes described herein or to known processes.

In the following non-limitative Examples all temperatures are indicated in degrees Centigrade.

EXAMPLE 1

4-(9,10-dihydro-4H-benzo[4,5]cyclohepta[1,2-b]thiophen-2-yl)-4-oxobutyric acid 11.0 g of succinic acid anhydride are dissolved in 220 cc of anhydrous methylene chloride with heating, the resulting solution is cooled to 20° and 30 g of aluminium chloride are added portionwise. After stirring for 15 minutes at room temperature, a solution of 22.0 g of 9,10-dihydro-4H-benzo[4,5]-cyclohepta[1,2-b]thiophene in 100 cc of anhydrous methylene chloride is added dropwise within 30 minutes, the resulting mixture is stirred for a further 45 minutes at room temperature and is poured on a mixture of 200 cc of concentrated hydrochloric acid and 200 g of ice. After adding 300 cc of methylene chloride, the entire mixture is heated for 15 minutes on a water bath, is cooled, the methylene chloride is removed and the aqueous phase is further extracted with methylene chloride. The acidic portion is extracted from the combined methylene chloride solutions with 0.5 normal caustic soda, the basic extract is acidified with 5 N hydrochloric acid and extracted with chloroform. The chloroform solutions are washed with water, dried over magnesium sulphate, filtered through active charcoal and evaporated to dryness. The title compound, obtained as solid residue, is recrystallized from dimethyl formamide/acetone. M.P. 202° to 203°.

The starting material may be obtained as follows:

25.0 g of sodium are added portionwise to a solution of 25.0 g of 9,10-dihydro-4H-benzo[4,5]cyclohepta[1,2-b]thiophen-4-one in 280 cc of anhydrous ethanol. After all the material is dissolved, the reaction mixture is heated to the boil for 2½ hours and the solvent is evaporated at reduced pressure. 500 cc of ice water and 200 cc of methylene chloride are slowly added to the evaporation residue, the organic phase is separated and the aqueous solution is again extracted with methylene chloride. The combined organic solutions are washed with water until neutral, dried over sodium sulphate and concentrated by evaporation. The residue is crystallized from ethanol. M.P. of 9,10-dihydro-4H-benzo[4,5]cyclohepta[1,2-b]thiophene: 117° to 119°.

EXAMPLE 2

4-(9,10-dihydro-4-oxo-4H-benzo[4,5]cyclohepta[1,2-b]thiophen-2-yl)-4-oxobutyric acid The title compound, having a M.P. of 167° to 168° (from ethanol/ether), is obtained by the process described in Example 1, from 12.2 g of succinic acid anhydride, 30 g of aluminium chloride and 15.0 g of 9,10-dihydro-4H-benzo[4,5]cyclohepta[1,2-b]thiophen-4-one in 320 cc of anhydrous methylene chloride.

EXAMPLE 3

5-(4-oxo-4H-benzo[4,5]cyclohepta[1,2-b]thiophen-2-yl)-5-oxovaleric acid

The title compound, having a M.P. of 149° to 151°, (recrystallized twice from acetone) is obtained by the process described in Example 1, from 13.0 g of glutaric acid anhydride, 30 g of aluminium chloride and 15.0 g of 4H-benzo[4,5]cyclohepta[1,2-b]thiophen-4-one in 350 cc of anhydrous methylene chloride.

The following (4H-benzo[4,5]cyclohepta[1,2-b]thiophen-2-yl)oxocarboxylic acid derivatives may also be obtained in a manner analogous to that described in Example 1, by reaction of the corresponding 4H-benzo[4,5]cyclohepta[1,2-b]thiophene derivatives with the corresponding dicarboxylic acid anhydrides:

| Ex.Nr. | Compound | Remarks, physical constants |
| --- | --- | --- |
| 4 | 4-(4-oxo-4H-benzo[4,5]cyclohepta[1,2-b]thiophen-2-yl)-4-oxobutyric acid | M.P. 233-234° (from acetone) |
| 5 | 4-(6-chloro-9,10-dihydro-4-oxo-4H-benzo[4,5]cyclohepta[1,2-b]thiophen-2-yl)-4-oxobutyric acid | M.P. 198-200° |
| 6 | 4-(9,10-dihydro-6-methyl-4-oxo-4H-benzo[4,5]cyclohepta[1,2-b]thiophen-2-yl)-4-oxobutyric acid | M.P. 177-179° |
| 7 | 4-(9,10-dihydro-8-methyl-4-oxo-4H-benzo[4,5]cyclohepta[1,2-b]thiophen-2-yl)-4-oxobutyric acid | |
| 8 | 4-(9,10-dihydro-7-methyl-4-oxo-4H-benzo[4,5]cyclohepta[1,2-b]thiophen-2-yl)-4-oxobutyric acid | |
| 9 | 4-(7-chloro-9,10-dihydro-4-oxo-4H-benzo[4,5]cyclohepta[1,2-b]thiophen-2-yl)-4-oxobutyric acid | |
| 10 | 4-(6-chloro-4-oxo-4H-benzo[4,5]cyclohepta[1,2-b]thiophen-2-yl)-4-oxobutyric acid | |
| 11 | 4-(4H-benzo[4,5]cyclohepta[1,2-b]thiophen-2-yl)-4-oxobutyric acid | |
| 12 | 4-(6-chloro-9,10-dihydro-4H-benzo[4,5]cyclohepta[1,2-b]thiophen-2-yl)-4-oxobutyric acid | |
| 13 | 4-(6-fluoro-9,10-dihydro-4-oxo-4H-benzo[4,5]cyclohepta- | |

| Ex.Nr. | Compound | Remarks, physical constants |
| --- | --- | --- |
|  | [1,2-b]thiophen-2-yl)-4-oxobutyric acid | |
| 14 | 6-(9,10-dihydro-4-oxo-4H-benzo[4,5]cyclohepta[1,2-b]-thiophen-2-yl)-6-oxocaproic acid | |
| 15 | 5-(9,10-dihydro-4-oxo-4H-benzo[4,5]cyclohepta[1,2-b]-thiophen-2-yl)-5-oxovaleric acid | M.P. 124–126° |

EXAMPLE 16 with the corresponding dicarboxylic acid monoalkyl ester halides:

| Ex.Nr. | Compound | Remarks, physical constants |
| --- | --- | --- |
| 18 | 4-(4-oxo-4H-benzo[4,5]cyclohepta[1,2-b]thiophen-2-yl-4-oxobutyric acid ethyl ester | |
| 19 | 4-(6-chloro-9,10-dihydro-4-oxo-4H-benzo[4,5]cyclohepta-]1,2-b]thiophen-2-yl)-4-oxobutyric acid methyl ester | |
| 20 | 4-(9,10-dihydro-6-methyl-4-oxo-4H-benzo[4,5]cyclohepta-[1,2-]thiophen-2-yl)-4-oxobutyric acid methyl ester | |
| 21 | 4-(9,10-dihydro-8-methyl-4-oxo-4H-benzo[4,5]cyclohepta-[1,2-b]thiophen-2-yl)-4-oxobutyric acid methyl ester | |
| 22 | 4-(9,10-dihydro-4H-benzo[4,5]cyclohepta[1,2-b]thiophen-2-yl)-4-oxobutyric acid ethyl ester | |
| 23 | 4-(6-chloro-4-oxo-4H-benzo[4,5]cyclohepta[1,2-b]thiophen-2-yl)-4-oxobutyric acid methyl ester | |
| 24 | 5-(4-oxo-4H-benzo[4,5]cyclohepta[1,2-b]thiophen-2-yl)-5-oxovaleric acid methyl ester | |
| 25 | 4-(6-fluoro-9,10-dihydro-4-oxo-4H-benzo[4,5]cyclohepta-[1,2-b]thiophen-2-yl)-4-oxobutyric acid methyl ester | |
| 26 | 6-(9,1C-dihydro-4-oxo-4H-benzo[4,5]cyclohepta[1,2-b]-thiophen-2-yl)-6-oxocaproic acid n-butyl ester | |

4-(9,10-dihydro-4-oxo-4H-benzo[4,5]cyclohepta[1,2-b]thiophen-2-yl)-4-oxobutyric acid methyl ester A solution of 6.3 cc of succinic acid monomethyl ester chloride in 100 cc of anhydrous carbon disulphide is added dropwise at 0° to a suspension of 10.0 g of 9,10-dihydro-4H-benzo[4,5]cyclohepta[1,2-b]thiophen-4-one and 30.0 g of anhydrous aluminium chloride in 200 cc of anhydrous carbon disulphide, the reaction mixture is stirred for a further 6 hours at room temperature, 23.3 g of tin tetrachloride are added dropwise thereto at 20° to 25° and stirring is continued at room temperature for 15 hours. The reaction mixture is subsequently heated to 50° for 2 hours, cooled, poured on 500 cc of 5 N hydrochloric acid and extracted with chloroform. The organic phases are washed with 5 N hydrochloric acid and with water, dried over magnesium sulphate and concentrated by evaporation. The evaporation residue is dissolved in 300 cc of methylene chloride, filtered through silica gel and evaporated to dryness. The title compound crystallizes from benzene/petroleum ether and is recrystallized once from ether. M.P. 97°–98°.

EXAMPLE 17

4-(4-oxo-4H-benzo[4,5]cyclohepta[1,2-b]thiophen-2-yl)-4-oxobutyric acid methyl ester The title compound is produced in a manner analogous to that described in Example 1, from 10.0 g of 4H-benzo[4,5]cyclohepta[1,2-b]thiophen-4-one, 30.0 g of anhydrous aluminium chloride and 23.3 g of tin tetrachloride and 6.3 cc of succinic acid monomethyl ester chloride in 300 cc of anhydrous carbon disulphide; the title compound is recrystallized from ether. M.P. 144°–145°.

The following (4H-benzo[4,5]cyclohepta[1,2-b]thiophen-2-yl)oxocarboxylic acid ester derivatives may also be obtained in a manner analogous to that described in Example 15 or 16, by reaction of the corresponding 4H-benzo[4,5]cyclohepta[1,2-b]thiophene derivatives

EXAMPLE 27

5-(4-oxo-4H-benzo[4,5]cyclohepta[1,2-b]thiophen-2-yl)-5-oxovaleric acid

A mixture of 10.0 g of 4H-benzo[4,5]cyclohepta[1,2-b]thiophen-4-one, 6.3 cc of succinic acid monomethyl ester chloride and 80 g of polyphosphoric acid is first stirred for one hour at 80° and then for 3 hours at 120°–130°, is cooled to 90°, 100 cc of water are added thereto and stirring is continued at the same temperature for a further hour. After cooling to room temperature, the reaction mixture is poured on 400 cc of ice water, is extracted with methylene chloride, the organic solutions are washed with water, dried over sodium sulphate and concentrated by evaporation. The title compound is crystallized from the evaporation residue with acetone and is recrystallized once. M.P. 149°–151°.

EXAMPLE 28

4-(9,10-dihydro-4-oxo-4H-benzo[4,5]cyclohepta[1,2-b]thiophen-2-yl)-4-oxobutyric acid [process variant (b)]

A solution of 3.0 g of 4-(9,10-dihydro-4-oxo-4H-benzo[4,5]cyclohepta[1,2-b]thiophen-2-yl)-4-oxobutyric acid methyl ester and 1.5 g of potassium hydroxide in 60 cc of dioxane and 30 cc of water is stirred at room temperature for 3 hours, dilution is effected with 200 cc of water and the pH of the solution is adjusted to 1 with concentrated hydrochloric acid at 10°–15°. The resulting title compound is extracted with methylene chloride, the organic solution is washed with water, dried over magnesium sulphate, concentrated by evaporation, and the title compound is recrystallized from dimethyl formamide/acetone. M.P. 167°–168°.

The (4H-benzo[4,5]cyclohepta[1,2-b]thiophen-2-yl)oxocarboxylic acid derivatives described in Examples 1 to 14 may also be obtained in a manner analogous to that described in Example 27, by hydrolysis of the corresponding (4H-benzo[4,5]cyclohepta[1,2-b]thiophen-2-yl)oxocarboxylic acid lower alkyl ester derivatives which may be produced in accordance with Example 15 or 16.

The compounds of formula I are useful as anti-phlogistic agents e.g. for the inhibition of exudation in oedemas as indicated by an inhibition of oedema formation in rats in the carrageen paw oedema test in vivo on p.o. administration of from about 5 to about 100 mg/kg animal body weight of the compounds, and in the subchronic granuloma cyst test on p.o. administration of from about 20 to about 100 mg/kg animal body weight of the compounds.

For this use the dosage will, of course, vary depending on the compound employed, mode of administration and treatment desired. However, in general, satisfactory results are obtained when administered at a daily dosage of from about 1 mg to about 100 mg/kg animal body weight, conveniently given in divided doses 2 to 4 times a day or in sustained release form. For the larger mammals, the total daily dosage is in the range from about 100 to about 1000 mg, and dosage forms suitable for oral administration comprise from about 25 mg to about 500 mg of the compounds admixed with a solid or liquid pharmaceutical carrier or diluent.

The compounds of formula I are furthermore useful as anti-arthritis agents, as indicated by an inhibition of swellings in the Freund adjuvant arthritis latent period test in rats on p.o. administration of from about 30 to about 100 mg/kg animal body weight of the compounds.

For this use the dosage will, of course, vary depending on the compound employed, mode of administration and treatment desired. However, in general, satisfactory results are obtained when administered at a daily dosage of from about 1 mg to about 100 mg/kg animal body weight, conveniently given in divided doses 2 to 4 times a day or in sustained release form. For the larger mammals, the total daily dosage is in the range from about 100 to about 1000 mg, and dosage forms suitable for oral administration comprise from about 25 mg to about 500 mg of the compounds admixed with a solid or liquid pharmaceutical carrier or diluent.

The compounds of formula I wherein $R_2$ is hydrogen may be administered in pharmaceutically acceptable salt form. Such salt forms exhibit the same order of activity as the free forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

In a group of compounds $R_1$ is in the 6 or 7 position of the tricyclic ring and preferably is hydrogen or halogen.

4-(9,10-dihydro-4-oxo-4H-benzo[4,5]cyclohepta-[1,2-b]thiophen-2-yl)-4-oxobutyric acid has been found to be especially interesting.

In one group of compounds $R_3$ and $R_4$ are hydrogen. In another group of compounds $R_3$ and $R_4$ together are oxygen.

What is claimed is:

1. A pharmaceutical composition useful in treating arthritis or oedema comprising a therapeutically effective amount of a compound of the formula

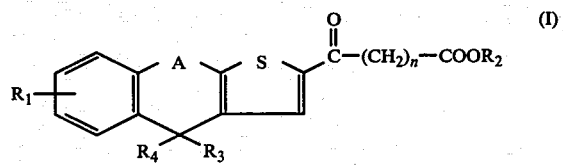

wherein
$R_1$ is hydrogen, halogen of atomic number from 9 to 35 or lower alkyl,
$R_2$ is hydrogen or lower alkyl, each of
$R_3$ and $R_4$ is hydrogen, or
$R_3$ and $R_4$ together are oxygen,
n is 2, 3 or 4, and
A is ethylene or vinylene,
or when $R_2$ is hydrogen alternatively in pharmaceutically acceptable salt form in association with a pharmaceutical carrier or diluent.

2. A pharmaceutical composition according to claim 1 comprising 25 to 500 milligrams of the compound per unit dosage.

3. A pharmaceutical composition according to claim 1 in which $R_3$ and $R_4$ together are oxygen.

4. A pharmaceutical composition according to claim 1 in which $R_1$ is in the 6- or 7-position.

5. A pharmaceutical composition according to claim 1 in which $R_1$ is hydrogen or halogen.

6. A pharmaceutical composition according to claim 1 in which A is ethylene.

7. A pharmaceutical composition according to claim 1 in which A is vinylene.

8. A pharmaceutical composition according to claim 1 in which the compound is 4-(9,10-dihydro-4-oxo-4H-benzo[4,5]cyclohepta[1,2-b]thiophen-2-yl)-4-oxobutyric acid.

9. A method of treating oedema and arthritis in animals which comprises administering to an animal in need of such treatment a therapeutically effective amount of a compound of the formula:

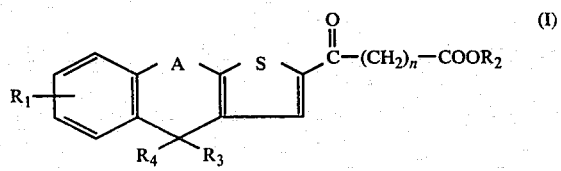

wherein
- $R_1$ is hydrogen, halogen of atomic number from 9 to 35 or lower alkyl,
- $R_2$ is hydrogen or lower alkyl, each of
- $R_3$ and $R_4$ is hydrogen, or
- $R_3$ and $R_4$ together are oxygen,
- n is 2, 3 or 4, and
- A is ethylene or vinylene, or when $R_2$ is hydrogen alternatively in pharmaceutical acceptable salt form.

10. A method according to claim 9 in which 100 to 1000 milligrams of the compound are administered daily.

11. A method according to claim 9 in which 25 to 500 milligrams of the compound are administered per unit dose.

12. A method according to claim 9 in which $R_3$ and $R_4$ together are oxygen.

13. A method according to claim 9 in which $R_1$ is in the 6- or 7-position.

14. A method according to claim 9 in which $R_1$ is hydrogen or halogen.

15. A method according to claim 9 in which A is ethylene.

16. A method according to claim 9 in which A is vinylene.

17. A method according to claim 9 in which the compound is 4-(9,10-dihydro-4-oxo-4H-benzo[4,5]cyclohepta[1,2-b]thiophen-2-yl)-4-oxobutyric acid.

* * * * *

UNITED STATES PATENT AND TRADEMARK OFFICE
CERTIFICATE OF CORRECTION

PATENT NO. : 4,137,323
DATED : Jan. 30, 1979
INVENTOR(S) : Jean-Michel Bastian

It is certified that error appears in the above-identified patent and that said Letters Patent are hereby corrected as shown below:

Page 1, item [30], please add the following Foreign Application Priority Data:

-- Oct. 10, 1973 [CH] Switzerland .........14396/73 --

Signed and Sealed this

Eighth Day of January 1980

[SEAL]

Attest:

SIDNEY A. DIAMOND

Attesting Officer

Commissioner of Patents and Trademarks